(12) United States Patent
Stiene

(10) Patent No.: US 11,712,365 B2
(45) Date of Patent: Aug. 1, 2023

(54) ORAL APPLIANCE

(71) Applicant: Janine Stiene, Mount Sinai, NY (US)

(72) Inventor: Janine Stiene, Mount Sinai, NY (US)

( * ) Notice: Subject to any disclaimer, the term of this patent is extended or adjusted under 35 U.S.C. 154(b) by 0 days.

(21) Appl. No.: 17/534,834

(22) Filed: Nov. 24, 2021

(65) Prior Publication Data

US 2023/0157860 A1    May 25, 2023

(51) Int. Cl.
*A61F 5/56*      (2006.01)
*A61C 7/08*      (2006.01)

(52) U.S. Cl.
CPC ............... *A61F 5/566* (2013.01); *A61C 7/08* (2013.01)

(58) Field of Classification Search
CPC .. A61F 5/56–566; A61F 5/00; A61C 7/00–36; A63B 71/08–085; A63B 2071/086; A63B 2071/088; A61M 16/0488–0497
See application file for complete search history.

(56) References Cited

U.S. PATENT DOCUMENTS

| | | | | |
|---|---|---|---|---|
| 3,224,441 A * | 12/1965 | Monaghan | ........... | A63B 71/085 433/37 |
| 4,608,974 A * | 9/1986 | Sicurelli, Jr. | ............. | A61F 5/00 128/869 |
| 4,718,662 A * | 1/1988 | North | ................... | A63B 23/032 482/11 |
| 4,997,182 A | 3/1991 | Kussick | | |
| 5,779,470 A * | 7/1998 | Kussick | ............. | A61F 5/05891 128/860 |
| 6,309,215 B1 * | 10/2001 | Phan | ....................... | A61C 9/00 433/24 |
| 2007/0240724 A1* | 10/2007 | Bergersen | ................ | A61C 7/08 128/861 |
| 2009/0130635 A1* | 5/2009 | Tortorici | .................. | A61C 7/10 433/7 |
| 2010/0266976 A1* | 10/2010 | Song | ........................ | A61C 7/14 433/8 |
| 2020/0138546 A1* | 5/2020 | Mohrlock | ................ | A61C 7/08 |
| 2021/0315729 A1* | 10/2021 | Huang | .................... | A61F 5/566 |

FOREIGN PATENT DOCUMENTS

CN           203576668 U     5/2014

OTHER PUBLICATIONS odlortho.com/product/retainer-with-tongue-crib, 2020, retrieved Nov. 24, 2021.

* cited by examiner

*Primary Examiner* — Michelle J Lee
(74) *Attorney, Agent, or Firm* — Frier Levitt, LLC

(57) ABSTRACT

An oral appliance covers maxillary dentition of a wearer and includes tongue tamers or spikes projecting posteriorly, and a lingual resting platform defining an aperture therethrough configured to receive a tip of the wearer's tongue. The oral appliance eliminates an anterior resting posture of the tongue and an abnormal anterior motion of the tongue, and deters noxious oral habits.

12 Claims, 3 Drawing Sheets

ORAL APPLIANCE

TECHNICAL FIELD

This disclosure relates to an oral appliance, and more particularly to an oral appliance for training proper lingual resting posture, dissuading the tongue from thrusting on or between the teeth, and deterring noxious oral habits.

BACKGROUND

An anterior lingual resting posture and/or an abnormal anterior motion of the tongue against the dentition and/or a noxious oral habit may cause deficits in one's oral facial development and have a negative effect on an individual's occlusion and palate, which can cause issues with one's speech, sleep, overall breathing, and/or temporomandibular joint function. Accordingly, there is a need to provide an oral appliance for training proper lingual and extinguish noxious oral habits.

SUMMARY

In accordance with the principles of the present disclosure, an oral appliance is provided that includes a shell, a plurality of tongue spikes formed on a posterior surface of the shell, and a platform projecting from the shell. The shell simulates maxillary dentition of a wearer such that the shell is configured to snugly fit over the maxillary dentition. The platform defines an aperture configured for receipt of the wearer's tongue.

In aspects, the shell may include at least six crowns configured to snugly fit over only corresponding left and right canines, lateral incisors, and central incisors of the maxillary dentition.

In aspects, the tongue spikes may project posteriorly from each of the crowns.

In aspects, the tongue spikes may project posteriorly from the posterior surface of the shell.

In aspects, the shell, the tongue spikes, and the platform may be monolithically formed with one another.

In aspects, the shell, the tongue spikes, and the platform may be fabricated from clear plastic.

In aspects, the aperture may be located posteriorly and above the tongue spikes.

In aspects, the platform may be configured to engage a palate of the wearer.

In accordance with further aspects of the present disclosure, an oral appliance is provided that includes a shell, a plurality of spikes projecting posteriorly from a posterior surface of the shell, and a platform projecting posteriorly from the shell. The shell includes six to eight crowns configured to snugly fit over corresponding maxillary dentition of a wearer. The spikes are configured to deter and/or prevent a tongue of the wearer from contacting the posterior surface of the shell as well as deter the wearer form engaging in any noxious oral habits. The platform defines an aperture therethrough configured for receipt of the wearer's tongue.

In aspects, the crowns may simulate corresponding left and right canines, lateral incisors, and central incisors of the maxillary dentition.

In aspects, the shell, the spikes, and the platform may be monolithically formed with one another.

In aspects, the shell, the spikes, and the platform may be fabricated from clear plastic.

In aspects, the aperture may be located posteriorly and above the spikes.

BRIEF DESCRIPTION OF THE DRAWINGS

The present disclosure will become more readily apparent from the specific description accompanied by the following drawings, in which.

DETAILED DESCRIPTION

Figure 1:
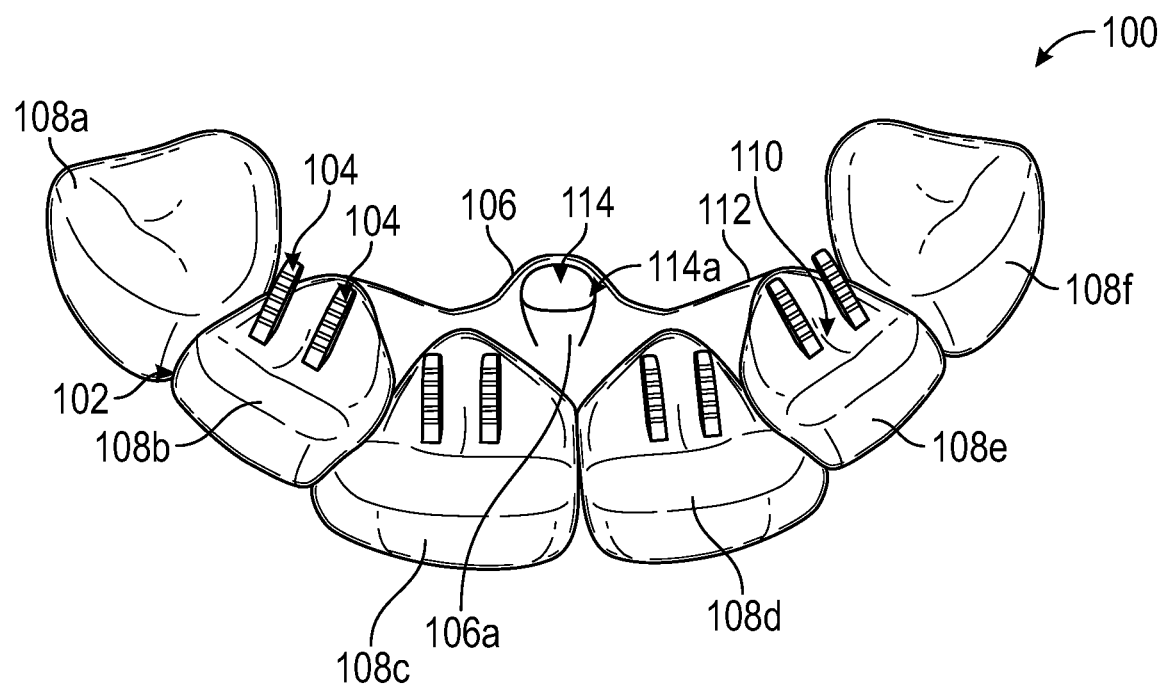
FIG. 1 is a bottom, perspective view illustrating an exemplary embodiment of an oral appliance.
Figure 2:
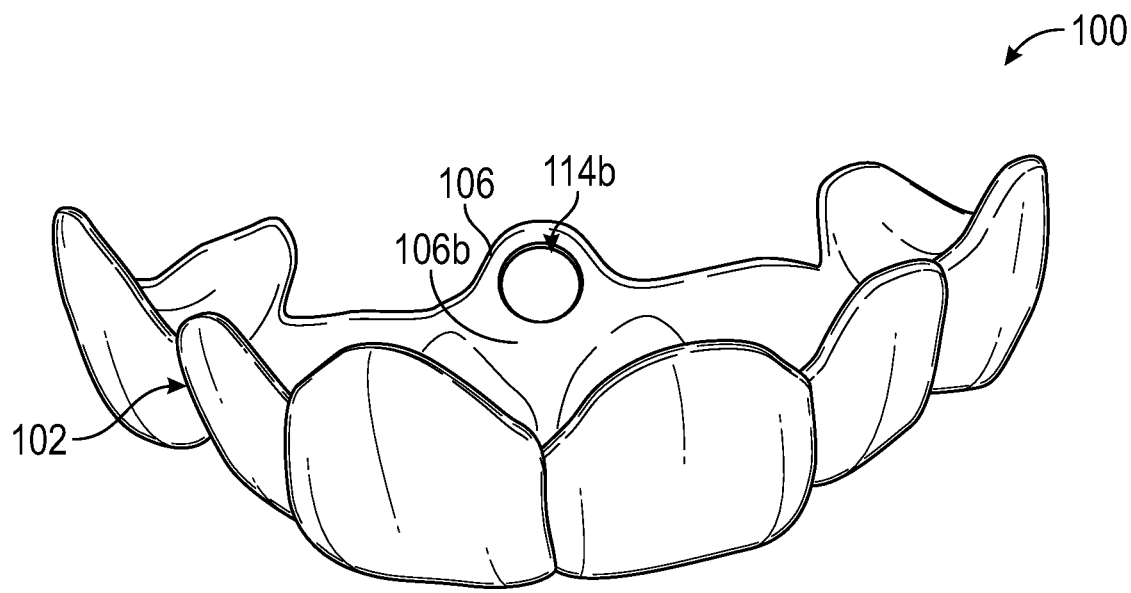
FIG. 2 is a front, perspective view of the oral appliance of FIG. 1.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "top" and "bottom" are relative and used only in the context to the other, and are not necessarily "superior" and "inferior."

As used herein, the terms parallel and perpendicular are understood to include relative configurations that are substantially parallel and substantially perpendicular up to about + or −15 degrees from true parallel and true perpendicular. As used herein, the term "posterior" refers to that portion of the oral appliance that is further from a wearer's face, and the term "anterior" refers to that portion of the oral appliance that is closer to the wearer's face.

The present disclosure generally provides a thin, custom plastic retainer-like appliance that fittingly engages the front upper 6-8 teeth of a wearer. The appliance has tongue spikes on the maxillary central and lateral incisors. The appliance also includes a designated hole for establishing lingual resting posture to eliminate an anterior resting posture of the tongue and abnormal anterior motion of the tongue, while eliminating any noxious oral habits. The appliance may be configured as a clear tooth aligner to promote proper resting posture and keep the tongue off of the dentition to support success and limit regression.

The oral appliance corrects and habituates proper lingual resting posture, which builds strength in the posterior portion of the oral cavity by improving an individual's overall resonance quality (hyponasal/hypernasal speech quality); supporting an open airway for individuals that suffer from sleep disordered breathing; and allowing the hard palate to mold to the proper shape and dimension by forming to the size and shape of the tongue, eliminating a narrow or "V" shaped arch, maximizing space in the nasal cavity for breathing purposes, and maximizing space in the nasal cavity for the resonance of sounds. The oral appliance may also improve overall intelligibility of the wearer by improving overall resonance; improving articulatory precision of most lingual alveolar and lingual palatal sounds; and improve an overall ability to manage saliva to decrease the "slushy sound" while articulating. The appliance may also improve nasal breathing by habituating a closed mouth posture by helping to filter air through the nasal cavity, limit the impact of at least one contributing cause of hypertrophic tonsils/adenoids, alter the shape of the face, limit the buildup of plaque, gingivitis, gum recession, cavities; improve overall occlusion by eliminating the tongue's ability to sit against the teeth at rest, and remove the opportunity of the tongue to sit in the space where a tooth is missing thus allowing the permanent dentition to come down in a timely manner; and reduce overall symptoms associated with TMJ/D by reducing teeth grinding, teeth clenching, and the incidence of "broken teeth," and deter an individual from engaging in any oral noxious habits, including but not limited to, thumb/finger sucking, tongue sucking, and nail biting. These and other advantageous of the presently disclosed appliance will be further elucidated herein.

With reference to FIGS. 1-4, an exemplary oral appliance 100 for detachable securement to maxillary dentition "D" is illustrated. The oral appliance 100 functions to, for example, train proper lingual resting posture and break any noxious oral habits. The oral appliance 100 may be configured as a custom-made dental retainer to maintain the proper alignment of a wearer's teeth, a clear aligner to adjust the wearer's dentition, or merely function to train proper lingual resting posture.

The oral appliance 100 generally includes a mouthpiece or shell 102 molded to fit over a wearer's (adult or child) maxillary dentition "D," tongue spikes 104 extending from the mouthpiece 102, and a lingual resting platform 106 extending from the mouthpiece 102. It is contemplated that each of the mouthpiece 102, the tongue spikes 104, and the lingual resting platform 106 are monolithically formed from the same material. For example, the oral appliance 100 may be fabricated entirely of clear or opaque plastic (e.g., acrylic, flexible polypropylene, polyvinylchloride, polyurethane resin, polyester).

Figure 3:
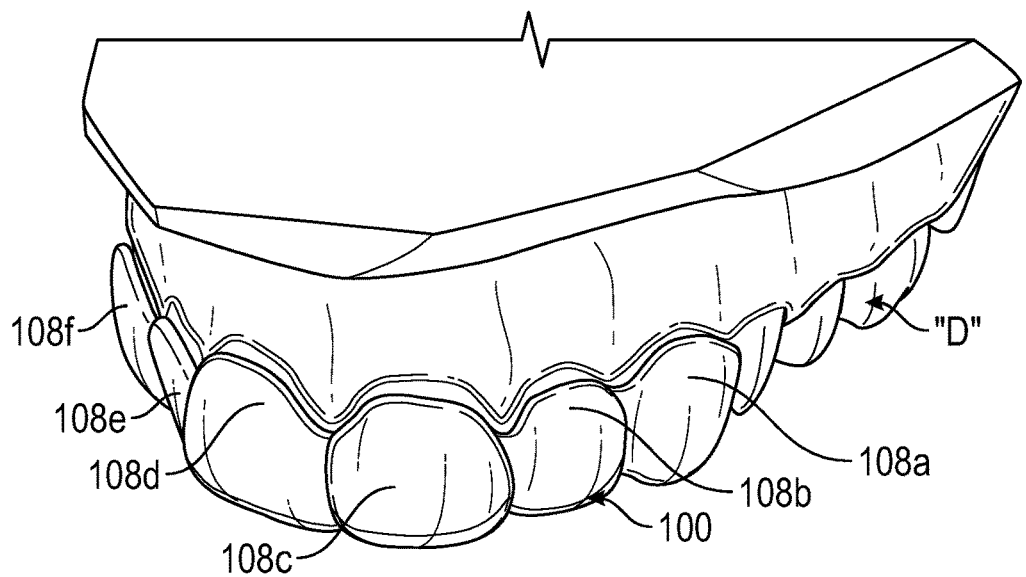
FIG. 3 is a perspective view of the oral appliance of FIG. 1 secured to maxillary dentition of a wearer.
Figure 4:
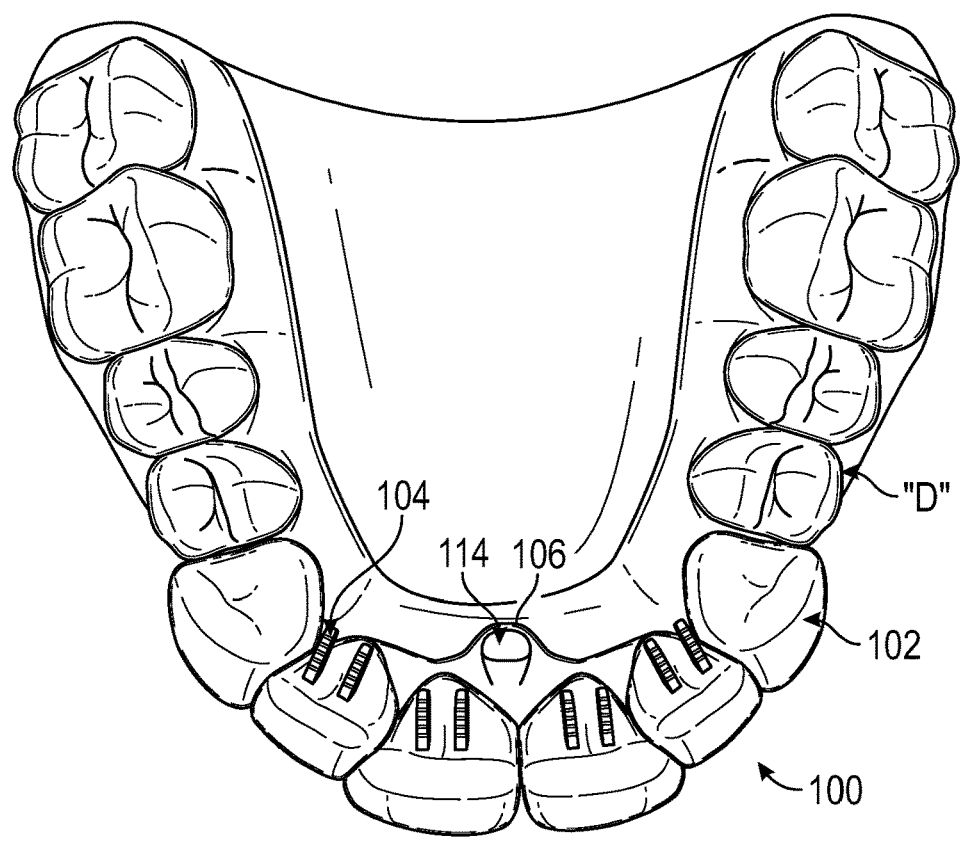
FIG. 4 is a bottom view illustrating the oral appliance of FIG. 1 secured to the maxillary dentition of the wearer.

As shown in FIGS. 3 and 4, the mouthpiece 102 is molded to fit over only the left and right canines, lateral incisors, central incisors, and in some aspects the first molars ("the anterior six to eight") of the dentition "D." As such, the mouthpiece 102 includes a plurality of crowns 108a, 108b, 108, 108d, 108e, 108f (collectively referred to herein as "108"), with each configured to snugly fit over a corresponding tooth of the anterior six (and in some aspects, the anterior eight). In aspects, the mouthpiece 102 may also include two additional crowns (not explicitly shown) that fit over the left and right first molars of the dentition "D." The mouthpiece 102 may be fabricated based on a dental impression or a digital scan of the patient's dentition "D." By only covering the anterior six to eight of the maxillary dentition "D," the tongue of a wearer of the oral appliance 100 will not be prohibited from moving anteriorly toward the posterior surface of the anterior six to eight since proper dental occlusion will be promoted.

The tongue spikes 104 of the oral appliance 100 project posteriorly from a posterior surface 110 of the mouthpiece 102 and are configured to cause pain or discomfort (without injuring) to the wearer's tongue when the tongue contacts the tongue spikes 104 at rest or while thrusting the tongue during swallowing. The tongue spikes 104 interfere with sucking by the wearer because the spikes 104 (tamers or spurs) act as a tactile cue and deterrent. In aspects, the tongue spikes 104 may project perpendicularly relative to the posterior surface 110 of the mouthpiece body.

Each crown 108 of the mouthpiece 102 may have one, two, or more tongue spikes 104. In other aspects, the tongue spikes 104 may be an elongated rod or any other suitable structure designed to cause pain or discomfort (without causing trauma) to the wearer's tongue sufficient to discourage, either consciously or unconsciously, continued contact of the tongue with the tongue spikes 104. Each of the tongue spikes 104 may further include a plurality of ridges defined along a length thereof configured to cause further discomfort for the user when their tongue engages or rubs against the tongue spikes 104 in a length-wise direction of the tongue spikes 104. In aspects, the tongue spikes 104 may be monolithically formed with or connected to the mouthpiece 102. In aspects, the spikes 104 may be customized to fit the patient's bite. For example, during scanning of the patient's upper and lower teeth, the bite may also be scanned and the spikes 104 may be adjusted accordingly to the specific amount of space from the upper teeth and lower teeth when the bite is closed. This will prevent the lower teeth from hitting the spikes 104 when the bite is closed.

The lingual resting platform 106 of the oral appliance 100 extends posteriorly and upwardly (e.g., in a direction into the mouth and towards the palate) from a central location of a posterior rim 112 of the mouthpiece 102. The platform 106 defines an aperture 114 therethrough configured to receive an anterior end of a tongue "T" (FIG. 6) of the wearer. The aperture 114 is configured to comfortably guide and encourage the anterior end of the tongue therein. The aperture 114 has an entrance opening 114a (FIG. 1) facing a mandibular side of the oral appliance 100 and an exit opening 114b (FIG. 2) facing a maxillary side of the oral appliance 100. The entrance opening 114a is configured to receive the anterior end of the tongue, whereby the tongue passes upwardly through the aperture 114 and out of the aperture 114 via the exit opening 114b. It is contemplated that the exit opening 114b may have a circular shape and the entrance opening 114a may be C-shaped. Other suitable shapes for the openings 114a, 114b are also contemplated. The platform 106 may have a ramped mandibular surface 106a (FIG. 1), and an opposing maxillary surface 106b (FIG. 2) configured to snugly engage a wearer's hard palate.

Figure 5:
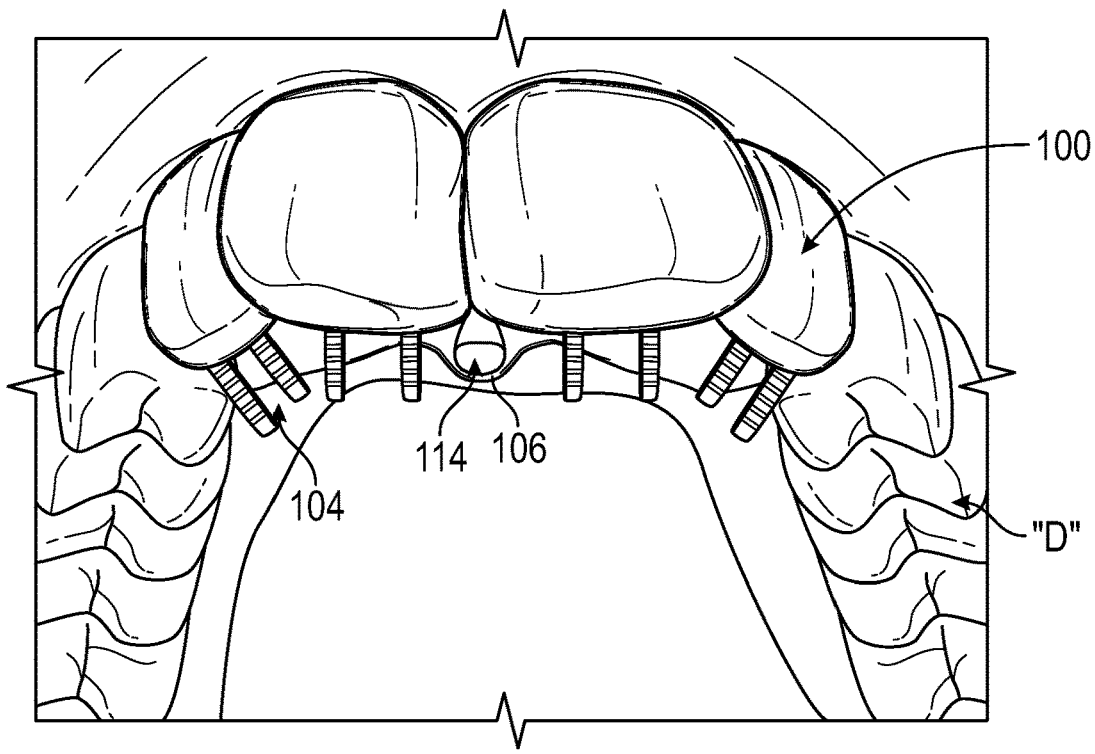
FIG. 5 is a bottom, perspective view illustrating a platform of the oral appliance of FIG. 1.

In use, as shown in FIG. 5, a wearer may insert the oral appliance 100 and wear the oral appliance 100 for a prescribed period of time, for example, at least about 30 minutes. While wearing the appliance 100, a wearer, out of habit, may thrust their tongue "T" into contact with the tongue spikes 104, whereby the discomfort experienced by the wearer will automatically direct the wearer's tongue 'T' toward the lingual resting platform 106 of the appliance 100.

Figure 6:
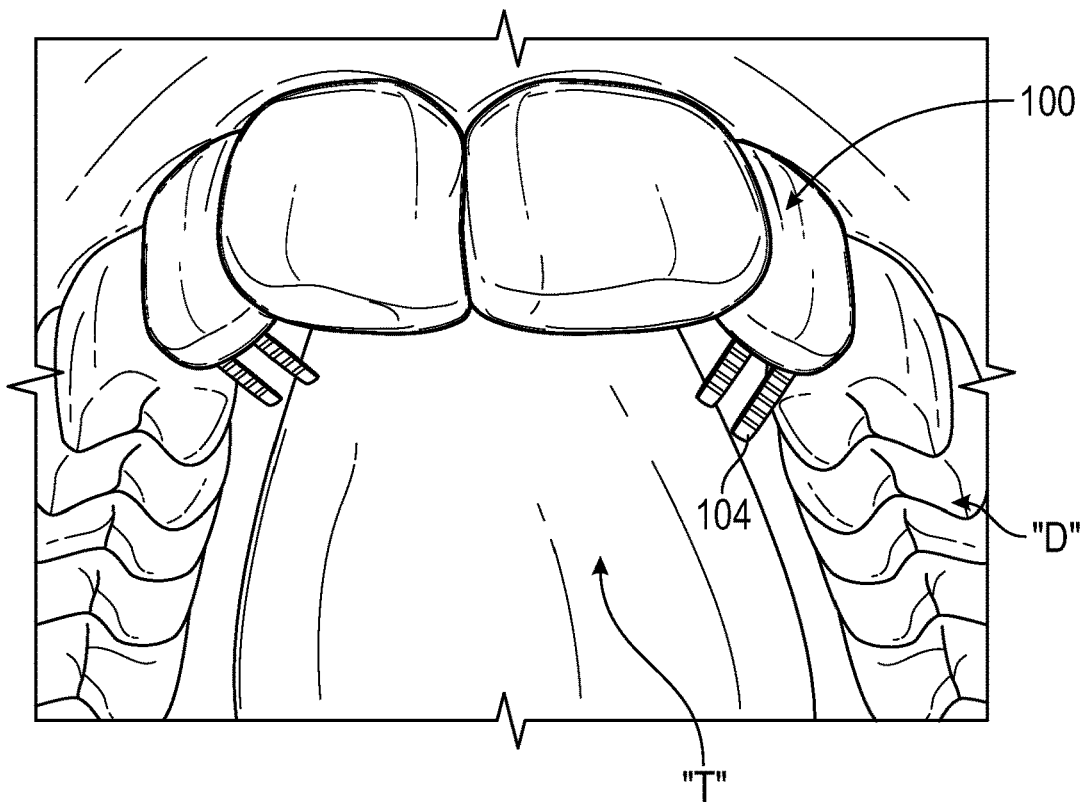
FIG. 6 is a front, perspective view illustrating a tongue of the wearer positioned on the platform of the oral appliance of FIG. 1.

The anterior end of the wearer's tongue "T" will be guided away from the tongue spikes 104 and into the aperture 114 where the tongue "T" will rest comfortably, as shown in FIG. 6. The appliance 100 allows for proper labial closure at rest and while swallowing, proper lingual motion on swallows, and proper lingual resting posture, whereby the posterior and anterior dentition is allowed to properly occlude, thus engaging the masseter muscles.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An oral appliance, comprising:
    a shell configured to simulate maxillary dentition of a wearer, wherein the shell includes a plurality of crowns which are configured to snugly fit over the maxillary dentition;
    a plurality of tongue spikes formed on a lingual surface of each crown of the shell projecting perpendicularly relative to the lingual surface;
    wherein each tongue spike further comprises an elongated rod having a plurality of ridges defined along a length thereof, the plurality of tongue spikes being configured to cause pain or discomfort to the tongue without injuring when the tongue contacts the plurality of tongue spikes and its ridges;
    a platform projecting from the shell, wherein the platform defines an aperture configured for receipt of the wearer's tongue; and
    wherein the aperture is C-shaped; and
    wherein the shell, the plurality of tongue spikes, and the platform are monolithically formed with one another.

2. The oral appliance according to claim 1, wherein the shell includes only six crowns.

3. The oral appliance according to claim 1, wherein the shell, the plurality of tongue spikes, and the platform are fabricated from clear plastic.

4. The oral appliance according to claim 1, wherein the aperture is located posteriorly and above the plurality of tongue spikes.

5. The oral appliance according to claim 1, wherein the platform is configured to engage a palate of the wearer.

6. An oral appliance, comprising:
    a shell configured to snugly fit over corresponding maxillary dentition of a wearer, the shell including a plurality of crowns;
    a plurality of spikes projecting perpendicularly from a lingual surface of each crown of the shell, each spike further comprising an elongated rod having a plurality of ridges defined along a length thereof and being configured to deter and/or prevent a tongue of the wearer from contacting the lingual surface of the shell due to pain or discomfort to the tongue without injuring when the tongue contacts the plurality of spikes and its ridges; and
    a platform projecting posteriorly from the shell, wherein the platform defines an aperture therethrough configured for receipt of the wearer's tongue; and
    wherein the aperture has an entrance opening which is C-shaped and an exit opening which is circular; and
    wherein the shell, the plurality of spikes, and the platform are monolithically formed with one another.

7. The oral appliance according to claim 6, wherein the plurality of crowns are configured to simulate corresponding left and right canines, lateral incisors, and central incisors of the maxillary dentition.

8. The oral appliance according to claim 6, wherein the shell, the plurality of spikes, and the platform are fabricated from clear plastic.

9. The oral appliance according to claim 6, wherein the aperture is located posteriorly and above the plurality of spikes.

10. The oral appliance according to claim 6, wherein the platform is configured to engage a palate of the wearer.

11. The oral appliance according to claim 6, wherein the aperture is aligned with a central longitudinal axis of the oral appliance, each of the plurality of spikes being offset from the central longitudinal axis.

12. The oral appliance according to claim 6, wherein the plurality of spikes are configured to be customized to fit the wearer's bite.

* * * * *